(12) United States Patent
Nomura et al.

(10) Patent No.: US 12,287,388 B2
(45) Date of Patent: Apr. 29, 2025

(54) MAGNETIC PARTICLE IMAGING DEVICE

(71) Applicant: Mitsubishi Electric Corporation, Tokyo (JP)

(72) Inventors: Kota Nomura, Tokyo (JP); Kodai Katagiri, Tokyo (JP); Tetsuya Matsuda, Tokyo (JP); Shun Tonooka, Tokyo (JP); Kazuki Yamauchi, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 244 days.

(21) Appl. No.: 17/912,042

(22) PCT Filed: Apr. 16, 2020

(86) PCT No.: PCT/JP2020/016734
§ 371 (c)(1),
(2) Date: Sep. 16, 2022

(87) PCT Pub. No.: WO2021/210135
PCT Pub. Date: Oct. 21, 2021

(65) Prior Publication Data
US 2023/0184862 A1    Jun. 15, 2023

(51) Int. Cl.
| G01R 33/563 | (2006.01) |
| G01R 33/3815 | (2006.01) |
| G01R 33/38 | (2006.01) |

(52) U.S. Cl.
CPC ... G01R 33/56375 (2013.01); G01R 33/3815 (2013.01); G01R 33/3804 (2013.01)

(58) Field of Classification Search
CPC .......... G01R 33/56375; G01R 33/3815; G01R 33/3804; G01R 33/035; G01R 33/16;
(Continued)

(56) References Cited

U.S. PATENT DOCUMENTS

| 2003/0085703 A1* | 5/2003 | Gleich | A61B 5/0515 |
| | | | 324/309 |
| 2006/0012371 A1* | 1/2006 | Laubacher | G01R 33/035 |
| | | | 324/322 |

(Continued)

FOREIGN PATENT DOCUMENTS

| JP | 1-94280 A | 4/1989 |
| JP | H0963831 | * 3/1997 |

(Continued)

OTHER PUBLICATIONS

International Search Report and Written Opinion mailed on Jul. 7, 2020, received for PCT Application PCT/JP2020/016734, filed on Apr. 16, 2020, 10 pages including English Translation.

*Primary Examiner* — Alexei Bykhovski
(74) *Attorney, Agent, or Firm* — XSENSUS LLP (57) ABSTRACT

A static magnetic field generator generates a non-magnetic field region. An AC magnetic field application instrument applies an AC magnetic field to the non-magnetic field region. A detection coil has an axis parallel to a direction of the AC magnetic field in order to detect a magnetization signal. A measuring instrument is connected to the detection coil. A resonance frequency variable device includes a capacitor connected in parallel to the detection coil in order to adjust a resonance frequency of the detection coil and the measuring instrument. A capacity of the capacitor is adjusted such that a resonance frequency of a closed circuit including the detection coil, the measuring instrument, and the resonance frequency variable device including the capacitor coincides with a frequency of a harmonic signal.

8 Claims, 7 Drawing Sheets

(58) Field of Classification Search
CPC ... G01R 33/1276; A61B 5/0515; A61B 5/055; A61B 2562/0223
See application file for complete search history.

(56) References Cited

U.S. PATENT DOCUMENTS

| | | |
|---|---|---|
| 2009/0085557 A1 | 4/2009 | Krozer et al. |
| 2011/0098558 A1* | 4/2011 | Weaver ............... G01R 33/4808 600/420 |
| 2011/0221438 A1* | 9/2011 | Goodwill ............. A61B 5/0515 324/301 |

FOREIGN PATENT DOCUMENTS

| | | |
|---|---|---|
| JP | 2003-199767 A | 7/2003 |
| JP | 2007-513339 A | 5/2007 |
| JP | 2009-534649 A | 9/2009 |
| JP | 2014-224741 A | 12/2014 |
| JP | 2017-44571 A | 3/2017 |
| WO | 2005/052619 A2 | 6/2005 |
| WO | 2007/120095 A1 | 10/2007 |

* cited by examiner

MAGNETIC PARTICLE IMAGING DEVICE

CROSS-REFERENCE TO RELATED APPLICATION

The present application is based on PCT filing PCT/JP2020/016734, filed Apr. 16, 2020, the entire contents of which are incorporated herein by reference.

TECHNICAL FIELD

The present disclosure relates to a magnetic particle imaging device.

BACKGROUND ART

There is known a method for imaging a distribution of magnetic particles (for example, super-paramagnetic iron oxide or the like) injected into an inspection object with a living body as a target (see, for example, PTL 1). This method is called "magnetic particle imaging (MPI)".

A magnetic particle imaging device generates a zero magnetic field region by generating magnetic fields that are directed opposite to each other, and applies an AC magnetic field by using a solenoid coil having a size capable of enclosing an inspection object and a reception coil. Here, outside the zero magnetic field region, a magnetic flux density does not change as long as a magnetic flux density of the magnetic particles is saturated, even when the AC magnetic field is applied. Whereas, in the zero magnetic field region, an influence of magnetization by a static magnetic field is small, and magnetization fluctuation occurs when the AC magnetic field is applied to the magnetic particles.

Due to the magnetization fluctuation of the magnetic particles in the zero magnetic field region, a change in a magnetic flux interlinking a detection coil occurs. This change in the magnetic flux is dependent on an amount of magnetic particles in the zero magnetic field region. The change in the magnetic flux interlinking the detection coil can be detected as a change in an induced electromotive force generated in the detection coil.

By using such a principle, when a signal generated in the detection coil is measured while the zero magnetic field region or the inspection object in the zero magnetic field region is moved in an imaging space, an image reflecting the distribution of the magnetic particles can be generated. Note that a device for realizing such magnetic particle imaging is called a magnetic particle imaging device.

An inspection object to be subjected to magnetic particle imaging often contains a very small amount of magnetic particles. When the amount of the contained magnetic particles is small, a magnetic signal to be measured becomes weak. Therefore, there is known a method of acquiring, by synchronous detection, an odd-order harmonic of an applied AC magnetic field on the basis of characteristics of a magnetic susceptibility curve of magnetic particles, and discriminating from external noise see, for example, PTL 2).

CITATION LIST

Patent Literature

PTL 1: Japanese Patent Laying-Open No. 2003-199767
PTL 2: Japanese Patent Laying-Open No. 2014-224741

SUMMARY OF INVENTION

Technical Problem

However, in the method of PTL 2, it is necessary to detect a signal associated with a change in magnetization of magnetic particles, with sufficiently higher sensitivity than noise in the same frequency band generated in a measurement circuit or the like. As an amount of the magnetic particles becomes smaller, magnitude of the signal associated with the change in magnetization of the magnetic particles becomes smaller.

An object of the present disclosure is to provide a magnetic particle imaging device capable of detecting a signal associated with a change in magnetization of magnetic particles with high sensitivity, even when an amount of magnetic particles in an inspection object becomes extremely small.

Solution to Problem

A magnetic particle imaging device to image a distribution of magnetic particles in an inspection object according to the present disclosure includes: a static magnetic field generator to generate a non-magnetic field region; an AC magnetic field application instrument to apply an AC magnetic field to the non-magnetic field region; and a magnetization distribution measuring instrument to measure a harmonic signal emitted from a magnetic particle in the non-magnetic field region. The magnetization distribution measuring instrument includes; a detection coil having an axis parallel to a direction of the AC magnetic field in order to detect a magnetization signal; a measuring instrument connected to the detection coil; and a resonance frequency variable device including a capacitor connected in parallel to the detection coil in order to adjust a resonance frequency of the detection coil and the measuring instrument. A capacity of the capacitor is adjusted such that a resonance frequency of a closed circuit including the detection coil, the measuring instrument, and the resonance frequency variable device coincides with a frequency of the harmonic signal.

Advantageous Effects of Invention

According to the present disclosure, a capacity of the capacitor is adjusted such that a resonance frequency of the closed circuit including the detection coil, the measuring instrument, and the resonance frequency variable device coincides with a frequency of the harmonic signal. This enables detection of a signal associated with a change in magnetization of the magnetic particles with high sensitivity, even when an amount of magnetic particles in the inspection object becomes extremely small.

DESCRIPTION OF EMBODIMENTS

Hereinafter, embodiments will be described with reference to the drawings.

First Embodiment

Figure 1:
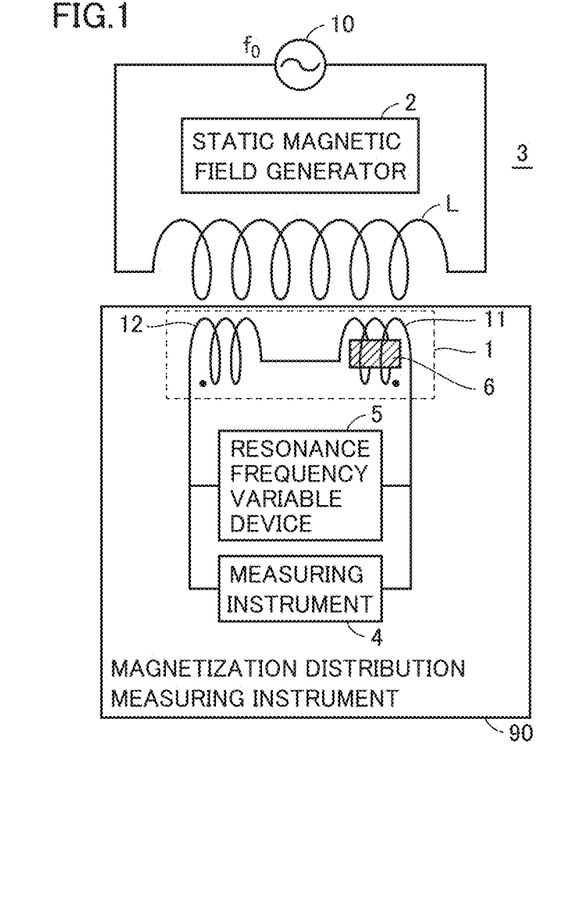
FIG. 1 is a diagram illustrating a configuration of a magnetic particle imaging device of a first embodiment.

FIG. 1 is a diagram illustrating a configuration of a magnetic particle imaging device of a first embodiment. As illustrated in FIG. 1, the magnetic particle imaging device includes a static magnetic field generator 2, an AC magnetic field application instrument 3, and a magnetization distribution measuring instrument 90.

Magnetization distribution measuring instrument 90 includes a detection coil 1 including a first detection coil 11 and a second detection coil 12, a measuring instrument 4, and a resonance frequency variable device 5.

Static magnetic field generator 2 forms a zero magnetic field region in an imaging region where an inspection object 6 is placed. Specifically, static magnetic field generator 2 includes two permanent magnets arranged to face each other with opposite directions of magnetization. In the present embodiment, a case will be described in which two permanent magnets arranged to face each other are used as static magnetic field generator 2, but a permanent magnet with two yokes in which magnetization is opposed by the yoke, or an electromagnet may be used instead of the two permanent magnets arranged to face each other.

In a case of performing magnetic particle imaging, a measurement position is scanned by changing a relative position of a zero magnetic field region formed by static magnetic field generator 2 with respect to inspection object 6. A method for changing the relative position includes: a method of applying a static magnetic field from outside to move the zero magnetic field region, a method of mechanically moving the static magnetic field generator, and a method of mechanically moving inspection object 6.

AC magnetic field application instrument 3 applies an AC magnetic field to an imaging region where inspection object 6 is placed. Specifically, AC magnetic field application instrument 3 includes an AC power supply 10 and a coil L connected to AC power supply 10. Here, in the drawing, detection coil 1 including first detection coil 11 and second detection coil 12 and coil L constituting AC magnetic field application instrument 3 are drawn in a developed manner. However, detection coil 1 including first detection coil 11 and second detection coil 12 and coil L constituting AC magnetic field application instrument 3 are arranged to coaxially overlap each other. A direction of an axis of detection coil 1 is parallel to a direction of an AC magnetic field generated by AC magnetic field application instrument 3.

In the present embodiment, detection coil 1 is configured by a first order differential coil in which first detection coil 11 and second detection coil 12 whose winding directions are opposite to each other are coaxially arranged. By using the first order differential coil, magnetic noise of an environment and of an induced electromotive force generated from the AC magnetic field applied by AC magnetic field application instrument 3 can be removed.

Inspection object 6 is installed inside first detection coil 11, and an AC magnetic field is applied by AC magnetic field application instrument 3. With the AC magnetic field applied by AC magnetic field application instrument 3, inspection object 6 generates a magnetic signal of a fundamental wave $f0$ and a magnetic signal of a harmonic signal ($n \times f0$) in accordance with a magnetic susceptibility curve of inspection object 6. These magnetic signals are measured as voltages by measuring instrument 4. In the present embodiment, since inspection object 6 is particles having superparamagnetism including iron oxide magnetic particles, the magnetic susceptibility curve of inspection object 6 has an odd function. Therefore, an intensity of an odd-order component ($n=2m+1$, $m=0, 1, 2, \ldots$) of the harmonic signal in inspection object 6 increases. The harmonic component that does not include an influence of fundamental wave $f0$ has a characteristic that noise is small and an SN ratio is high.

Resonance frequency variable device 5 includes a capacitor having a capacitance. Detection coil 1 including first detection coil 11 and second detection coil 12, measuring instrument 4, and resonance frequency variable device 5 including the capacitor form a closed circuit for measurement of a harmonic signal generated from inspection object 6. Here, the closed circuit means a circuit in which a switch or the like is closed and a path through which a current flows is established in the electric circuit.

Therefore, when resonance frequency variable device 5 and detection coil 1 are connected in parallel, a resonance circuit is configured by a combined inductance and a combined capacitor on the closed circuit. A resonance frequency of the resonance circuit is determined by an inductance and a capacitor on the resonance circuit. For example, in a case where a third harmonic $3f0$ is used as a detection signal when magnetic particle imaging is performed, third harmonic $3f0$ can be adjusted to have a resonance frequency of the closed circuit by measuring the inductance and the capacitor in detection coil 1 and measuring instrument 4 on the closed circuit and selecting a capacitance C of resonance frequency variable device 5. As a result, a signal intensity of the targeted harmonic signal can be maximized.

Figure 2:
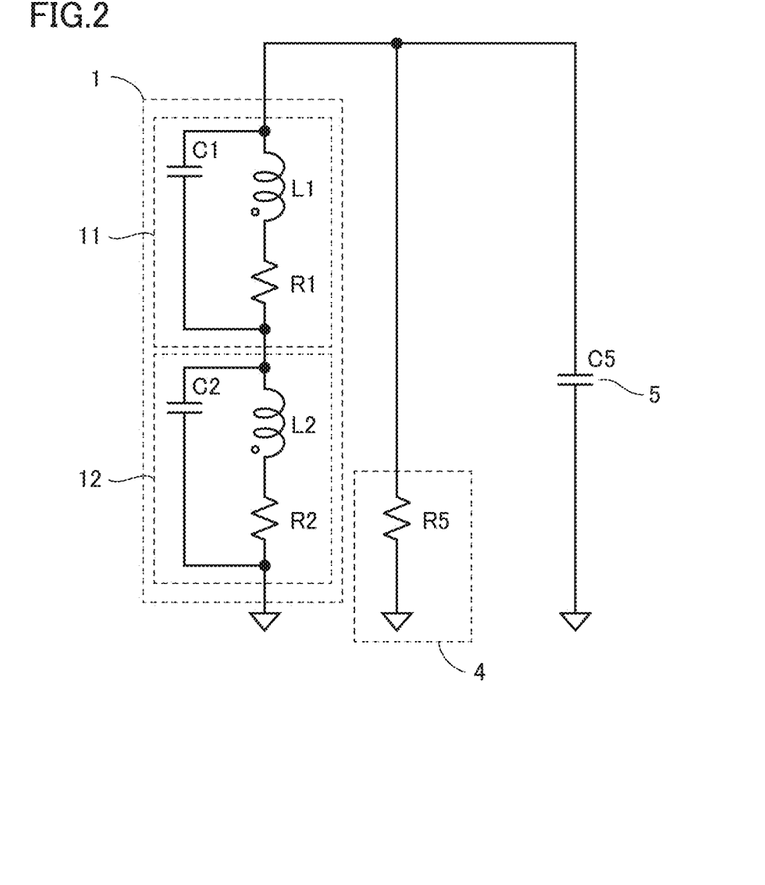
FIG. 2 is a diagram illustrating an equivalent circuit of the magnetic particle imaging device of the first embodiment.

FIG. 2 is a diagram illustrating an equivalent circuit of the magnetic particle imaging device of the first embodiment. FIG. 2 illustrates an equivalent circuit of a circuit including detection coil 1 including first detection coil 11 and second detection coil 12, AC magnetic field application instrument 3, measuring instrument 4, and resonance frequency variable device 5.

A winding density of detection coil 1 needs to be increased in order to increase detection sensitivity. For example, the winding density of detection coil 1 is several hundred turns/mm. Therefore, a stray capacity generated between the windings of detection coil 1 greatly affects the resonance frequency.

In first detection coil 11, a stray capacity C1 generated between windings of first detection coil 11 is connected in parallel to a resistance component R1 and an inductance L1 connected in series in first detection coil 11. In second detection coil 12, a stray capacity C2 generated between windings of second detection coil 12 is connected in parallel to a resistance component R2 and an inductance L2 connected in series in second detection coil 12. Assuming that detection coil 1 is configured as a first order differential coil, it is assumed that a signal of the AC magnetic field applied from AC magnetic field application instrument 3 is not generated.

AC magnetic field application instrument 3 (coil L and AC power supply 10) is bound to inductance L1 and inductance L2. Due to an effect of a differential coil, a signal between AC magnetic field application instrument 3 and inductance L1 and the signal between AC magnetic field application instrument 3 and inductance L2 are canceled. Therefore, AC magnetic field application instrument 3 (the coil L and AC power supply 10) is not visible from a detection system. A signal of magnetic particles is excited only to inductance L1, and this signal is acquired.

A result of analyzing the equivalent circuit illustrated in FIG. 2 will be described assuming that a magnetization signal from inspection object 6 is bound to inductance L1 of first detection coil 11 to generate an induced electromotive force.

Figure 3:
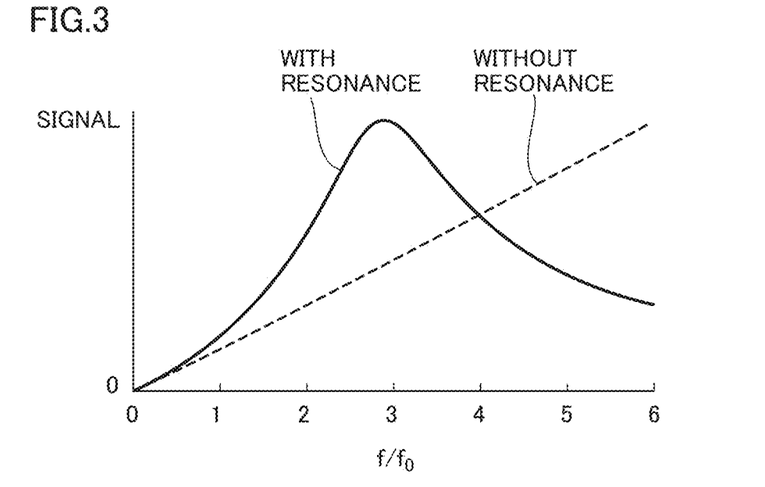
FIG. 3 is a schematic graph illustrating a frequency characteristic of a signal voltage detected by a measuring instrument 4 in the equivalent circuit of the magnetic particle imaging device illustrated in FIG. 2.

FIG. 3 is a schematic graph illustrating a frequency characteristic of a signal voltage detected by measuring instrument 4 in the equivalent circuit of the magnetic particle imaging device illustrated in FIG. 2.

A result of analyzing a frequency characteristic of a voltage applied to an internal resistance R5 of measuring instrument 4 is illustrated.

A broken line in FIG. 3 indicates a frequency characteristic in a circuit to which resonance frequency variable device 5 is not electrically connected. In a circuit to which resonance frequency variable device 5 is not electrically connected, a resonance frequency is in a high frequency band of 20 or higher. Therefore, sensitivity is low in a frequency band of about the third harmonic which is targeted by magnetic particle imaging.

A solid line in FIG. 3 represents an analysis result in a case where capacitance C of resonance frequency variable device 5 is selected so as to have a resonance frequency of third harmonic 3f0. A voltage applied to internal resistance R5 of measuring instrument 4 is maximized near third harmonic 3f0 by resonance frequency variable device 5.

In this manner, by selecting capacitance C of resonance frequency variable device 5, a frequency of a harmonic signal required for magnetic particle imaging can be made coincide with a resonance frequency of the closed circuit including detection coil 1, measuring instrument 4, and resonance frequency variable device 5. This can increase an amplitude of a signal detected by measuring instrument 4. As a result, even when an amount of magnetic particles in the target inspection object becomes extremely small, a signal associated with a change in magnetization of the magnetic particles can be detected with high sensitivity.

Modification 1 of First Embodiment

When an image is reconstructed, an information amount for acquiring a dependence of a spatial resolution and a density is increased in a case where a plurality of harmonic components can be acquired, as compared with a case where one harmonic component is acquired. It is conceivable to provide a plurality of resonance frequency variable devices 5 selected to resonate with harmonics such as third and fifth harmonics.

Figure 4:
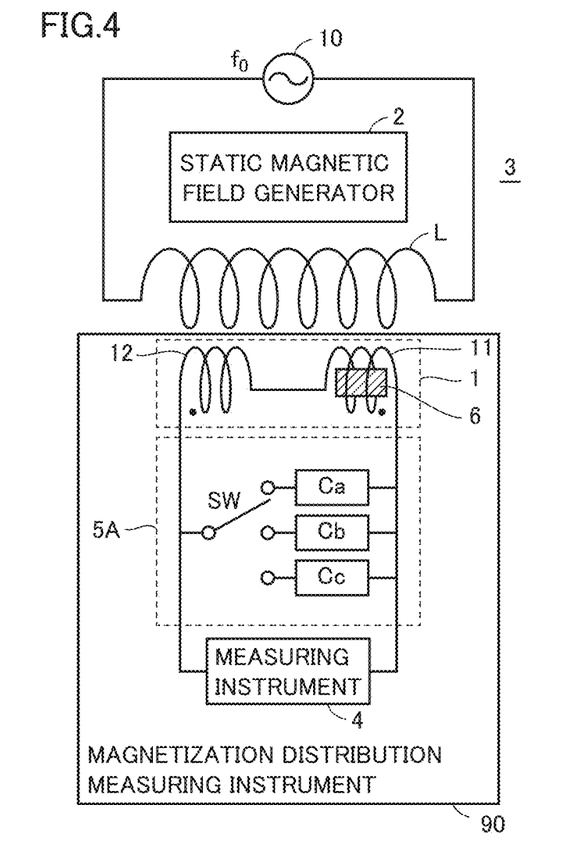
FIG. 4 is a diagram illustrating a configuration of a magnetic particle imaging device according to a modification of the first embodiment.

FIG. 4 is a diagram illustrating a configuration of a magnetic particle imaging device according to a modification of the first embodiment. A resonance frequency variable device 5A of the magnetic particle imaging device according to this modification includes: a plurality of capacitors Ca, Cb, and Cc connected in parallel; and a switching circuit SW to switch a capacitor connected to detection coil 1 among the plurality of capacitors Ca, Cb, and Cc.

Capacities of the plurality of capacitors Ca, Cb, and Cc are adjusted such that a resonance frequency of the closed circuit including detection coil 1, measuring instrument 4, and one of the plurality of capacitors Ca, Cb, and Cc coincides with a frequency of one of a plurality of harmonic signals.

For example, a capacity of capacitor Ca is adjusted such that a resonance frequency of the closed circuit including detection coil 1, measuring instrument 4, and capacitor Ca coincides with a frequency of third harmonic 3f0. A capacity of capacitor Cb is adjusted such that a resonance frequency of the closed circuit including detection coil 1, measuring instrument 4, and capacitor Cb coincides with a fifth harmonic 5f0 frequency. A capacity of capacitor Cc is adjusted such that a resonance frequency of the closed circuit including detection coil 1, measuring instrument 4, and capacitor Cc coincides with a frequency of a seventh harmonic 7f0.

Second Embodiment

Figure 5:
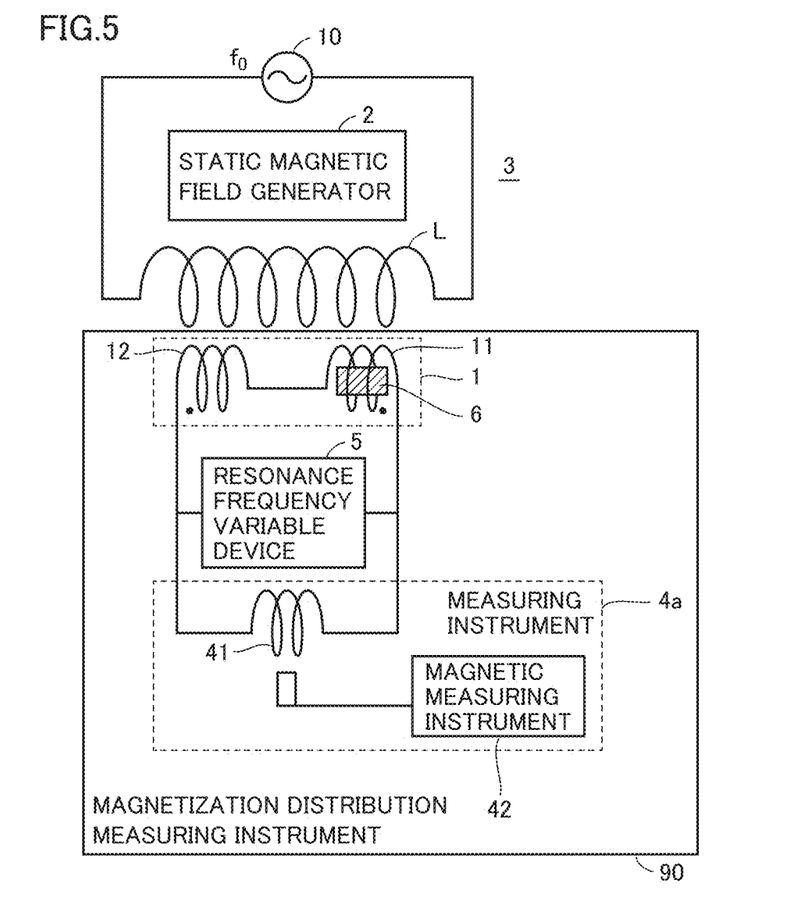
FIG. 5 is a diagram illustrating a configuration of a magnetic particle imaging device of a second embodiment.

FIG. 5 is a diagram illustrating a configuration of a magnetic particle imaging device of a second embodiment.

In the present embodiment, a measuring instrument 4a includes a transfer coil 41 and a magnetic measuring instrument 42. In the first embodiment, a magnetic signal from inspection object 6 detected by first detection coil 11 is propagated to measuring instrument 4 as a voltage signal. Whereas, in the present embodiment, by connecting transfer coil 41, a circuit closed only by a detection coil 1, transfer coil 41, and a resonance frequency variable device 5 is formed. A magnetic signal generated from an inspection object 6 propagates in the closed circuit as a current. Transfer coil 41 is energized with a current based on the magnetic signal generated from inspection object 6, and transfer coil 41 excites a magnetic field based on the energizing current.

Magnetic measuring instrument 42 detects the magnetic signal generated from inspection object 6 by measuring the magnetic field excited by transfer coil 41. This causes magnetic particle imaging to be performed. As magnetic measuring instrument 42, a SQUID magnetic detection device, a flux gate sensor, or an MI effect element can be used.

In the present embodiment, the closed circuit including detection coil 1, transfer coil 41, and resonance frequency variable device 5 is formed. By selecting a capacitance C of resonance frequency variable device 5, a frequency of a harmonic signal required for magnetic particle imaging can be made coincide with a resonance frequency of the closed circuit including detection coil 1, transfer coil 41, and resonance frequency variable device 5.

Figure 6:
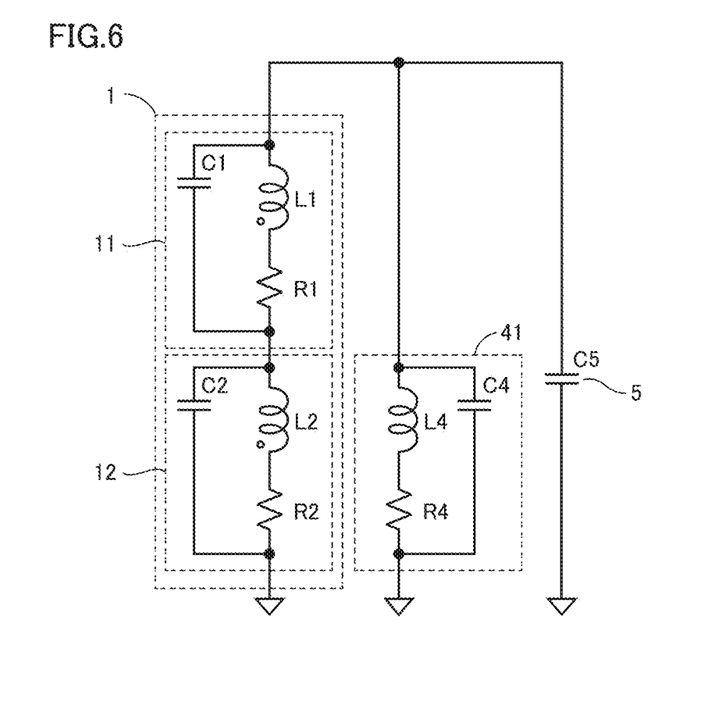
FIG. 6 is a diagram illustrating an equivalent circuit of the magnetic particle imaging device of the second embodiment.

FIG. 6 is a diagram illustrating an equivalent circuit of the magnetic particle imaging device of the second embodiment.

The equivalent circuit includes detection coil 1 including a first detection coil 11 and a second detection coil 12, an AC magnetic field application instrument 3, transfer coil 41, and resonance frequency variable device 5.

Figure 7:
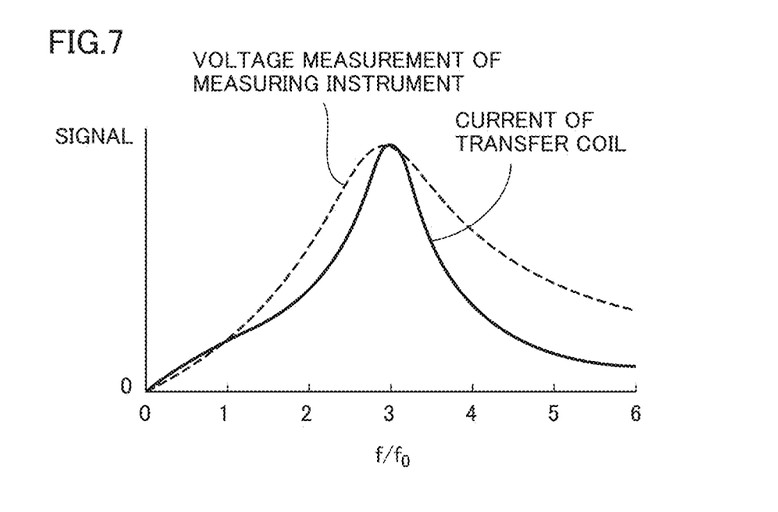
FIG. 7 is a graph illustrating a frequency characteristic of a current flowing through an inductance L4 of a transfer coil 41 obtained by analysis using the equivalent circuit illustrated in FIG. 6.

FIG. 7 is a graph illustrating a frequency characteristic of a current flowing through an inductance L4 of transfer coil 41 obtained by analysis using the equivalent circuit illustrated in FIG. 6.

In FIG. 7, a frequency characteristic of a result analyzed by the magnetic particle imaging device of the first embodiment is indicated by a broken line, and a result analyzed by the magnetic particle imaging device of the second embodiment is indicated by a solid line.

As in the first embodiment, a general measuring instrument to measure a voltage has a high internal resistance (for example, 10 MΩ is used in this analysis), a half-value width of a resonance peak is widened, and a peak intensity is lowered. Whereas, in the present embodiment, the intensities cannot be compared since each peak intensity is made dimensionless. However, in the present embodiment, since a resistance component on a resonance circuit is reduced by transfer coil 41, it can be confirmed that a half-value width of a resonance peak is narrowed.

As described above, according to the present embodiment, by using transfer coil 41, a resistance component on the circuit to be resonated can be reduced, so that the half-value width of the resonance peak can be narrowed. This can lower frequency band sensitivity around the target harmonic, so that an S/N ratio of a signal detected by magnetic measuring instrument 42 can be increased.

Third Embodiment

Figure 8:
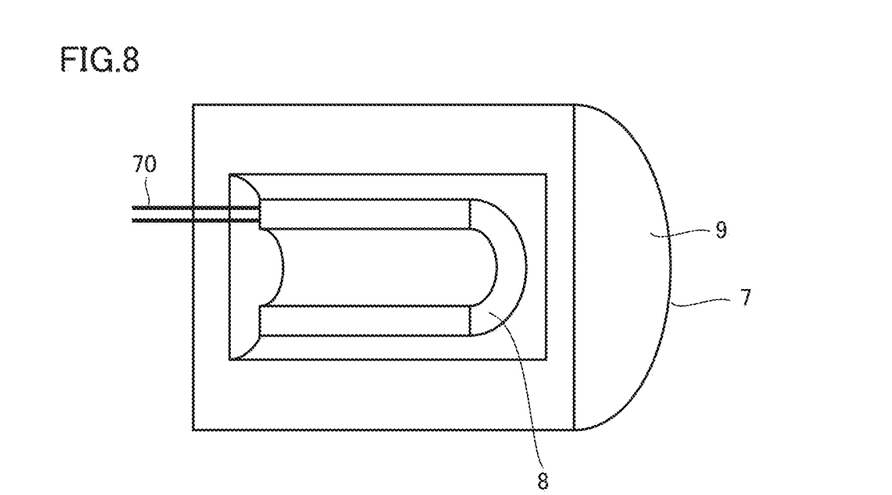
FIG. 8 is a coil cross-sectional view of a magnetic particle imaging device of a third embodiment.

FIG. 8 is a cross-sectional view of a superconducting coil 7 constituting a detection coil 1 and a transfer coil 41 included in a magnetic particle imaging device of a third embodiment. As described in the second embodiment, if it is possible to reduce a resistance component on a closed circuit including detection coil 1 including a first detection coil 11 and a second detection coil 12, a measuring instrument 4, and a resonance frequency variable device 5, which constitute the magnetic particle imaging device, a Q value represented by resonance peak intensity/peak width can be increased. Therefore, in the present embodiment, the resistance component is lowered by using superconducting coil 7 as detection coil 1 and transfer coil 41, which are main factors of the resistance component on the closed circuit. Superconducting Coil 7 Includes a Superconductor 8 and a Cooler 9.

Superconductor 8 is desirably an oxide-based high-temperature superconductor exhibiting a superconducting characteristic at a liquid nitrogen temperature of 77 K or more. Cooler 9 is configured by, for example, a cryocooler of stainless steel or the like. Superconductor 8 is immersed and cooled in liquid nitrogen in cooler 9.

By electrically connecting the inside and the outside of cooler 9 with a normal conducting cable 70, only winding portions of detection coil 1 and transfer coil 41 can be handled as a superconductor. As a result, for example, detection coil 1, transfer coil 41, and resonance frequency variable device 5 can be connected by normal conducting cable 70.

Figure 9:
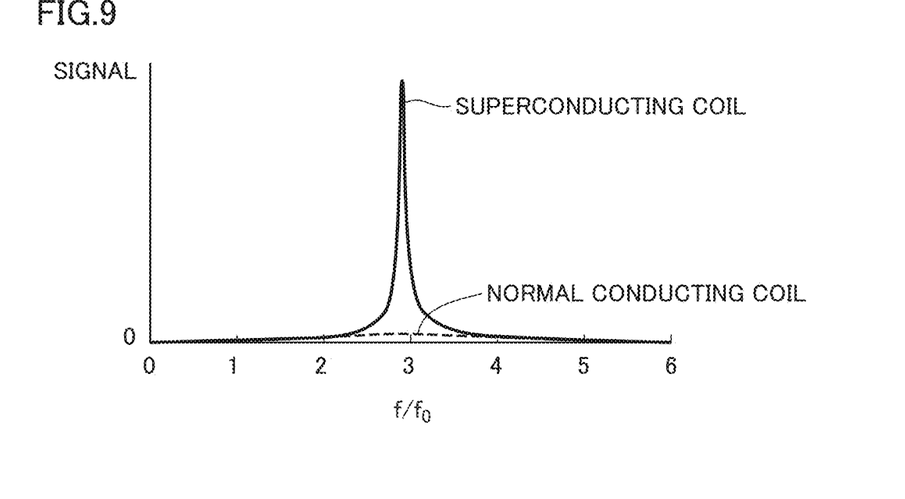
FIG. 9 is a schematic graph illustrating a frequency characteristic obtained by the magnetic particle imaging device of the third embodiment.

FIG. 9 is a schematic graph illustrating a frequency characteristic obtained by the magnetic particle imaging device of the third embodiment. A solid line in FIG. 9 indicates an analysis result when a resistance component is reduced to about 1/300 by using superconducting coil 7 as inductances L1, L2, and L4 on the equivalent circuit illustrated in FIG. 6. An analysis result when inductances L1, L2, and L4 are normal conductors is indicated by a broken line. In this analysis, it can be confirmed that a quality factor (Q) value is improved by 30 times or more due to a decrease in the resistance component.

In the present embodiment, by configuring detection coil 1 and transfer coil 41 with superconducting coil 7, it is possible to reduce the resistance component of these coils having a large number of windings. This can reduce a half-value width of a resonance peak, and can also increase a peak intensity. As a result, detection sensitivity of the magnetic particle imaging device is enhanced.

In the above embodiment, both of detection coil 1 and transfer coil 41 are superconducting coil 7, but the present invention is not limited thereto. Any one of detection coil 1 and transfer coil 41 may be superconducting coil 7. As a result, as compared with a case where both of detection coil 1 and transfer coil 41 are normal conducting coils, it is possible to reduce the resistance component of these coils.

Fourth Embodiment

Figure 10:
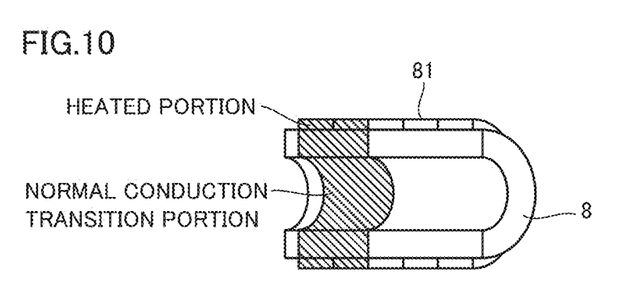
FIG. 10 is a coil cross-sectional view of a magnetic particle imaging device of a fourth embodiment.

FIG. 10 is a cross-sectional view of a superconducting coil 7 constituting a detection coil 1 and a transfer coil 41 included in a magnetic particle imaging device of a fourth embodiment. As illustrated in FIG. 10, a heater 81 thermally connected to superconducting coil 7 is provided in the vicinity of a superconductor 8 constituting superconducting coil 7.

Heater 81 heats only a predetermined portion of superconducting coil 7 to cause transition of only the predetermined portion to a normal conduction band.

For example, heater 81 may be configured by a plurality of systems of nichrome wires to control a heating region by dividing the heating region. In addition, a region to be subjected to the normal conduction transition may be controlled by adjusting a heating amount of heater 81. By controlling the heating region energized by heater 81, only a heated portion of superconductor 8 can be subjected to the normal conduction transition.

This makes it possible to vary a resistance component on a closed circuit including detection coil 1 including a first detection coil 11 and a second detection coil 12, a measuring instrument 4, and a resonance frequency variable device 5, which constitute the magnetic particle imaging device. As a result, a Q value of a resonance circuit can be adjusted without incorporating a new element on the circuit.

Figure 11:
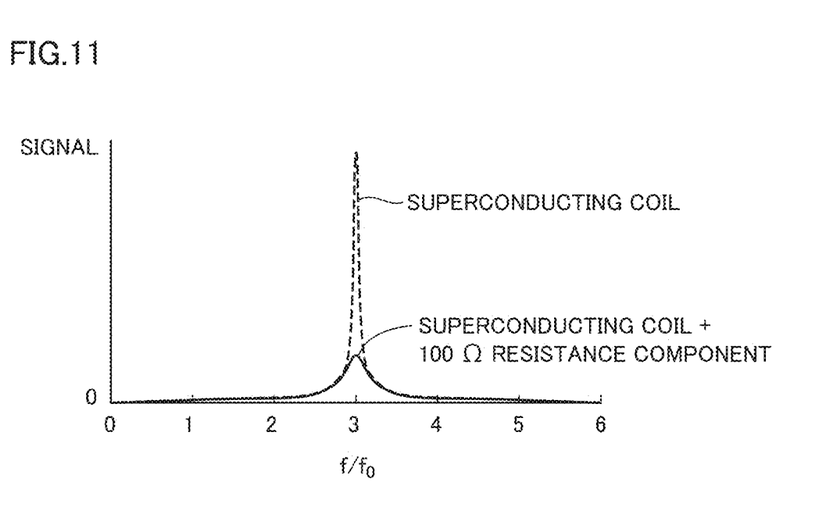
FIG. 11 is a schematic graph illustrating a frequency characteristic obtained by the magnetic particle imaging device of the fourth embodiment.

FIG. 11 is a schematic graph illustrating a frequency characteristic obtained by the magnetic particle imaging device of the fourth embodiment.

A broken line in FIG. 11 is the same as the solid line in FIG. 9. A solid line in FIG. 11 indicates an analysis result in a case where about 1/3 of a region of superconductor 8 of superconducting coil 7 is subjected to the normal conduction transition. When heater 81 causes a part of superconductor 8 to be subjected to the normal conduction transition, resistance on the circuit can be changed. As a result, sensitivity and a half-value width of a resonance peak can be adjusted with respect to a change in electrical characteristic or the like due to insertion of an inspection object.

It is to be understood that the embodiments that have been disclosed herein are not restrictive, but are illustrative in all respects. The scope of the present disclosure is defined not by the description above but by the claims, and it is intended to include all modifications within the meaning and scope equivalent to the claims.

REFERENCE SIGNS LIST

1: detection coil, 2: static magnetic field generator, 3: AC magnetic field application instrument, 5, 5A: resonance frequency variable device, 6: inspection object, 7: superconducting coil, 8: superconductor, 9: cooler, 10: AC power supply, 11: first detection coil, 12: second detection coil, 41: transfer coil, 42: magnetic measuring instrument, 70: normal conducting cable, 81: heater, 90: magnetization distribution measuring instrument, Ca, Cb, Cc: capacitor, L: coil, SW: switching circuit

The invention claimed is:

1. A magnetic particle imaging device to image a distribution of a magnetic particle in an inspection object, the magnetic particle imaging device comprising:
a static magnetic field generator to generate a non-magnetic field region;
an alternating current (AC) magnetic field application instrument to apply an AC magnetic field to the non-magnetic field region; and
a magnetization distribution measuring instrument to measure a harmonic signal emitted from a magnetic particle in the non-magnetic field region,
wherein the magnetization distribution measuring instrument includes:
a detection coil having an axis parallel to a direction of the AC magnetic field in order to detect a magnetization signal;
a measuring instrument connected to the detection coil; and
a resonance frequency variable device including a capacitor connected in parallel to the detection coil in order to adjust a resonance frequency of the detection coil and the measuring instrument, and
a capacity of the capacitor is adjusted such that a resonance frequency of a closed circuit including the detection coil, the measuring instrument, and the resonance frequency variable device coincides with a frequency of the harmonic signal,
the measuring instrument includes:
a transfer coil to be energized with a current based on a magnetic signal generated from the inspection object, and to excite a magnetic field based on an energizing current; and
a magnetic measuring instrument to measure a magnetic field excited by the transfer coil, and
the closed circuit includes the detection coil, the transfer coil, and the resonance frequency variable device.

2. The magnetic particle imaging device according to claim 1, wherein
the resonance frequency variable device includes:
a plurality of capacitors including the capacitor, the plurality of capacitors being connected in parallel with each other; and
a switching circuit to switch one of the plurality of capacitors to be connected to the detection coil, and
a capacity of each of the plurality of the capacitors is adjusted such that a resonance frequency of a closed circuit including the detection coil, the measuring instrument, and the one of the plurality of the capacitors coincides with a frequency of one of a plurality of harmonic signals.

3. The magnetic particle imaging device according to claim 1, wherein both or any one of the detection coil and the transfer coil is a superconducting coil.

4. The magnetic particle imaging device according to claim 3, wherein
the superconducting coil includes a superconductor and a cooler, and
the detection coil, the transfer coil, and the resonance frequency variable device are connected by a normal conducting cable.

5. The magnetic particle imaging device according to claim 4, wherein
the superconducting coil includes a heater thermally connected to the superconducting coil, and
the heater heats only a predetermined portion of the superconducting coil to cause transition of only the predetermined portion to a normal conduction band.

6. The magnetic particle imaging device according to claim 3, wherein
the superconducting coil includes a heater thermally connected to the superconducting coil, and
the heater heats only a predetermined portion of the superconducting coil to cause transition of only the predetermined portion to a normal conduction band.

7. The magnetic particle imaging device according to claim 1, wherein the transfer coil is arranged in parallel with the capacitor in the resonance frequency variable device and in parallel with the detection coil.

8. The magnetic particle imaging device according to claim 1, wherein the magnetic measuring instrument includes a flux gate sensor or a Magnetic Impedance (MI) effect element.

* * * * *